(12) United States Patent
Müller et al.

(10) Patent No.: US 6,245,792 B1
(45) Date of Patent: Jun. 12, 2001

(54) FUNGICIDAL MIXTURE

(75) Inventors: Bernd Müller, Frankenthal; Hubert Sauter, Mannheim; Eberhard Ammermann, Heppenheim; Gisela Lorenz, Hambach; Siegfried Strathmann, Limburgerhof; Reinhold Saur, Böhl-Iggelheim; Klaus Schelberger, Gönnheim; Joachim Leyendecker, Ladenburg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/702,123

(22) Filed: Oct. 31, 2000

Related U.S. Application Data

(62) Division of application No. 09/171,648, filed as application No. PCT/EP97/02047 on Oct. 22, 1998.

(30) Foreign Application Priority Data

| | | |
|---|---|---|
| Apr. 26, 1996 | (DE) | 196 16 717 |
| Apr. 29, 1996 | (DE) | 196 17 075 |
| Apr. 29, 1996 | (DE) | 196 17 074 |
| May 9, 1996 | (DE) | 196 18 676 |

(51) Int. Cl.⁷ .................. A01N 55/00; A01N 43/50; A01N 43/54; A01N 43/56; A01N 43/64
(52) U.S. Cl. ................ 514/383; 514/63; 514/259; 514/399; 514/407
(58) Field of Search ................ 514/383, 407, 514/259, 63, 399

(56) References Cited

U.S. PATENT DOCUMENTS 5,260,326 * 11/1993 Sauter et al. .............. 514/383

FOREIGN PATENT DOCUMENTS

9601256 * 1/1996 (WO).
9661258 * 1/1996 (WO).

* cited by examiner

Primary Examiner—Allen J. Robinson
(74) Attorney, Agent, or Firm—Keil & Weinkauf

(57) ABSTRACT

A composition comprising effective amounts of a) a carbamate (I)

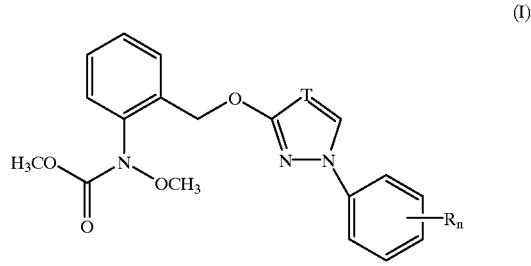

wherein T is CH or N, n is 0, 1 or 2, and R is halogen, $C_1$–$C_4$-alkyl or $C_1$–$C_4$-haloalkyl, where the radicals R are identical or different if n is 2, and b) an azole (IV) as defined in the specification which exhibits a synergistically enhanced fungicidal effect is described.

7 Claims, No Drawings

FUNGICIDAL MIXTURE

This is a divisional application of application Ser. No. 09/171,648, filed on Oct. 22, 1998, which is a National Stage application under 35 U.S.C. 371, based on International Application No. PCT/EP 97/02,047, filed Apr. 23, 1997.

The present invention relates to fungicidal mixtures which comprise a) a carbamate of the formula I

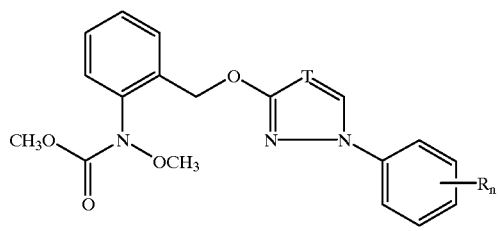

I where T is CH or N, n is 0, 1 or 2 and R is halogen, $C_1$–$C_4$-alkyl or $C_1$–$C_4$-haloalkyl, it being possible for the radicals R to be different when n is 2, and at least one compound from the groups consisting of b)–d):

b) oxire ethers of the formula II

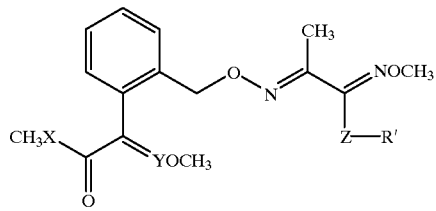

(II)

where the substituents have the following meanings:
X is oxygen or amino (NH);
Y is CH or N;
Z is oxygen, sulfur, amino (NH) or $C_1$–$C_4$-alkylamino (N—$C_1$–$C_4$-alkyl);
R' is $C_1$–$C_6$-alkyl, $C_1$–$C_6$-haloalkyl, $C_3$–$C_6$-alkenyl, $C_2$–$C_6$-haloalkenyl, $C_3$–$C_6$-alkynyl, $C_3$–$C_6$-haloalkynyl, $C_3$–$C_6$-cycloalkylmethyl, or is benzyl which can be partially or fully halogenated and/or have attached to it one to three of the following radicals: cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

c.1) the oxime ether carboxylate of the formula IIIa

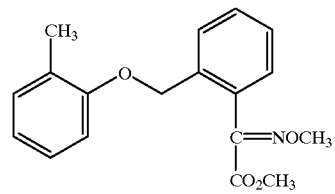

(IIIa)

c.2) the oxime ether carboxamide of the formula IIIb

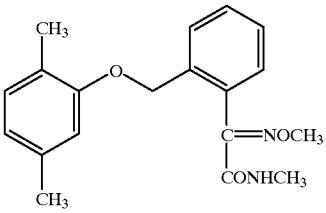

(IIIb)

c.3) the methoxyacrylate of the formula IIIc,

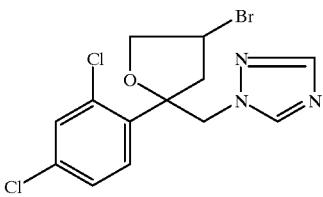

(IIIc)

and/or d) an azole derivative IV selected from the group of the compounds IV.1 to IV.17

1-[(2RS,4RS;2RS,4SR)-4-bromo-2-(2,4-dichlorophenyl)tetrahydrofuryl]-1H-1,2,4-triazole (IV.1)

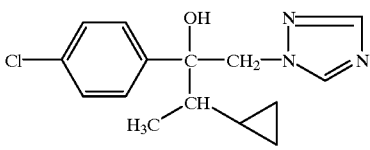

2-(4-chlorophenyl)-3-cyclopropyl-1-(1H-1,2,4-triazol-1-yl)-butan-2-ol (IV.2)

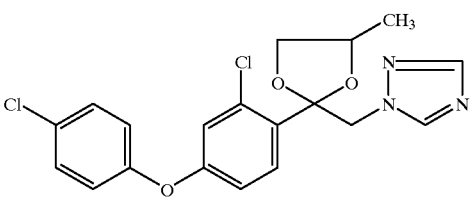

(+)-4-chloro-4-[4-methyl-2-(1H-1,2,4-triazol-1-ylmethyl)-1,3-dioxolan-2-yl)phenyl 4-chlorophenyl ether (IV.3)

(E)-(R,S)-1-(2,4-dichlorophenyl)-4,4-dimethyl-2-(1H-1,2,4-triazol-1-yl)pent-1-en-3-ol (IV.4)

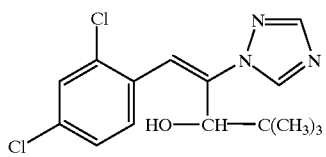

(Z)-2-(1H-1,2,4-triazol-1-ylmethyl)-2-(4-fluorophenyl)-3-(2-chlorophenyl)oxirane (IV.5)

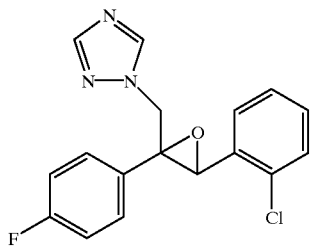

4-(4-chlorophenyl)-2-phenyl-2-(1H-1,2,4-triazolylmethyl)-butyronitrile (IV.6)

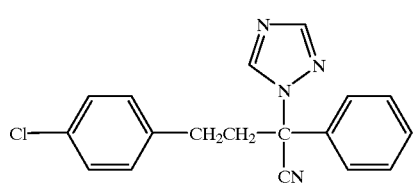

3-(2,4-dichlorophenyl)-6-fluoro-2-(1H-1,2,4-triazol-1-yl)quinazolin-4(3H)-one (IV.7)

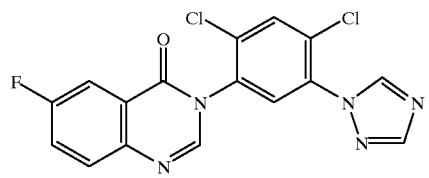

bis(4-fluorophenyl)(methyl)(1H-1,2,4-triazol-1-ylmethyl)-silane (IV.8)

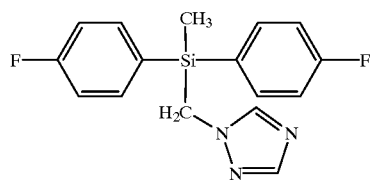

(R,S)-2-(2,4-dichlorophenyl)-1-(1H-1,2,4-triazol-1-yl)-hexan-2-ol (IV.9)

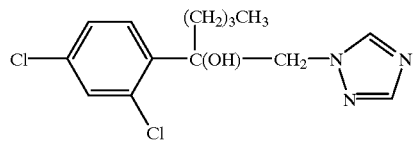

(1RS,5RS;1RS,5SR)-5-(4-chlorobenzyl)-2,2-dimethyl-1-(1H-1,2,4-triazol-1-ylmethyl) cyclopentanol (IV.10)

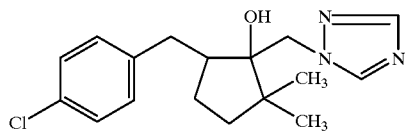

N-propyl-N-[2-(2,4,6-trichlorophenoxy)ethyl] imidazol-1-carboxamide (IV.11)

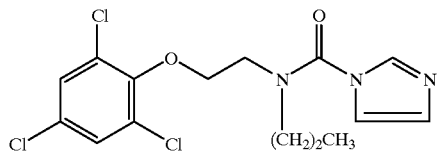

(+)-1-[2-(2,4-dichlorophenyl)-4-propyl-1,3-dioxolan-2-yl-methyl]-1H-1,2,4-triazole (IV.12)

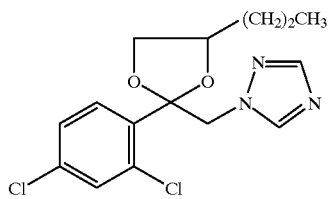

(R,S)-1-(4-chlorophenyl)-4,4-dimethyl-3-(1H-1,2,4-triazol-1-ylmethyl)pentan-3-ol (IV.13)

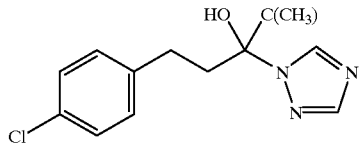

(+)-2-(2,4-dichlorophenyl)-3-(1H-1,2,4-triazolyl) propyl 1,1,2,2-tetrafluoroethyl ether (IV.14)

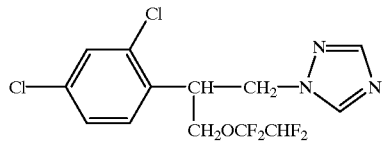

(E)-1-[1-[[4-chloro-2-(trifluoromethyl)phenyl]imino]-2-propoxyethyl]-1H-imidazol (IV.15)

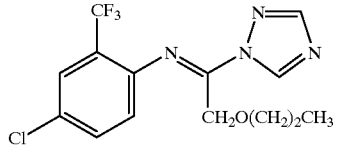

(RS)-2,4'-difluoro-α-(1H-1,2,4-triazol-1-ylmethyl) benzhydroyl [sic] alcohol (IV.16)

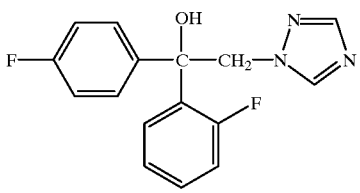

2-p-chlorophenyl-2-(1H-1,2,4-triazol-1-ylmethyl) hexanonitrile (IV.17)

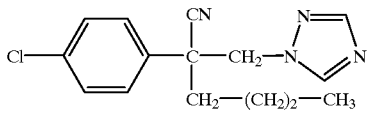

in a synergistically active amount.

Moreover, the invention relates to methods of controlling harmful fungi with mixtures of the compounds I, II, III and IV and to the use of the compounds I, II, III and IV for the preparation of such mixtures.

The compounds of the formula I, their preparation and their action against harmful fungi have been disclosed in the literature (WO-A 96/01,256 and WO-A 96/01,258).

The compounds II are described in the literature as fungicides and insecticides (German Application No. 19 528 651.0).

The compounds IIIa (EP-A 253 213), IIIb (EP-A 477 631) and the compound IIIc (EP-A 382 375), their preparation and their action against harmful fungi have also been disclosed.

The azole derivatives IV, their preparation and their action against harmful fungi are known to the expert from the literature:

IV.1: common name: bromuconazole, Proc. Br. Crop Prot. Conf.—Pests Dis., 5–6, 439 (1990);

IV.2: common name: cyproconazole, U.S. Pat. No. 4,664, 696;

IV.3: common name: difenoconazole, GB-A 2,098,607;

IV.4: common name: diniconazole, CAS RN [83657-24-3];

IV.5: common name (proposed): epoxiconazole, EP-A 196 038;

IV.6: common name: fenbuconazole (proposed), EP-A 251 775;

IV.7: common name: fluquinconazole, Proc. Br. Crop Prot. Conf.—Pests Dis., 5–3, 411 (1992);

IV.8: common name: flusilazole, Proc. Br. Crop Prot. Conf.—Pests Dis., 1, 413 (1984);

IV.9: common name: hexaconazole, CAS RN [79983-71-4];

IV.10: common name: metconazole, Proc. Br. Crop Prot. Conf.—Pests Dis., 5–4, 419 (1992);

IV.11: common name: prochloraz, U.S. Pat. No. 3,991,071;

IV.12: common name: propiconazole, GB-A 1,522,657;

IV.13: common name: tebuconazole, U.S. Pat. No. 4,723, 984;

IV.14: common name: tetraconazole, Proc. Br. Crop Prot. Conf.—Pests Dis., 1, 49 (1988);

IV.15: common name: triflumizole, JP-A 79/119,462

IV.16: common name: flutriafol, CAS RN [76674-21-0]

IV.17: common name: myclobutanil, CAS RN [88671-89-0].

It was an object of the present invention to provide mixtures which display an improved activity against harmful fungi combined with a reduced total amount of active ingredients applied (synergistic mixtures) with a view to reducing the rates of application and to improving the spectrum of action of the known compounds.

Accordingly, we have found that this object is achieved by the mixture defined at the outset. Moreover, we have found that better control of the harmful fungi is possible by applying the compounds I and II or III or IV simultaneously together or separately or by applying the compounds I and II or III or IV in succession than when the individual compounds are used.

In particular, the formula I represents carbamates in which the combination of the substituents corresponds to one line of the table which follows:

TABLE 1

| No. | T | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

The compounds I.12, I.23, I.32 and I.38 are especially preferred.

The general formula II particularly represents oxime ethers where X is oxygen and Y is CH or X is amino and Y is N.

Compounds II which are furthermore preferred are those where Z is oxygen.

Compounds II which are equally preferred are those where R' is alkyl and benzyl.

Compounds II which are particularly preferred with a view to their use in the synergistic mixtures according to the invention are those compiled in the tables which follow:

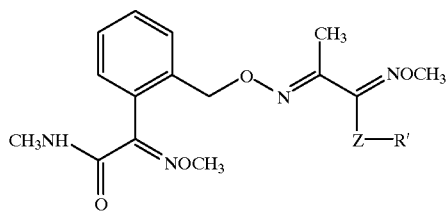
(IIA)

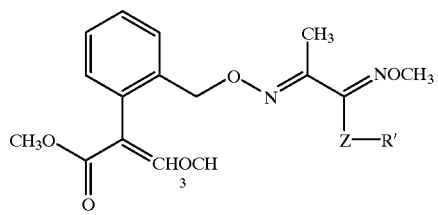
(IIB)

TABLE B

| No. | ZR' |
| --- | --- |
| II.1 | O—CH$_2$CH$_2$CH$_3$ |
| II.2 | O—CH(CH$_3$)$_2$ |
| II.3 | O—CH$_2$CH$_2$CH$_2$CH$_3$ |
| II.4 | O—CH(CH$_3$)CH$_2$CH$_3$ |
| II.5 | O—CH$_2$CH(CH$_3$)$_2$ |
| II.6 | O—C(CH$_3$)$_3$ |
| II.7 | S—C(CH$_3$)$_3$ |
| II.8 | O—CH(CH$_3$)CH$_2$CH$_2$CH$_3$ |
| II.9 | O—CH$_2$C(CH$_3$)$_3$ |
| II.10 | O—C(Cl)=CCl$_2$ |
| II.11 | O—CH$_2$CH=CH—Cl (trans) |
| II.12 | O—CH$_2$—C(CH$_3$)=CH$_2$ |
| II.13 | O—CH$_2$—(cyclopropyl) |
| II.14 | O—CH$_2$—C$_6$H$_5$ |
| II.15 | O—CH$_2$-[4-F—C$_6$H$_4$] |

Relative to the C=Y or C=CH or C=N double bonds, the compounds of the formulae I, II and III can exist in the E or in the Z configuration (relative to the carboxylic acid function). Accordingly, they can be used in the mixture according to the invention in each case as pure E or Z isomers or as an E/Z isomer mixture. The E/Z isomer mixture or the Z isomer are preferably used, the Z isomer being especially preferred.

The C=N double bonds of the oxime ether groups in the side chain of the compounds I can exist in each case as the pure E or Z isomers or as E/Z isomer mixtures. The compounds I can be used in the mixtures according to the invention both as isomer mixtures and as pure isomers. Preferred with a view to their use are, in particular, compounds of the formula I where the terminal oxime ether group of the side chain is in the cis configuration (OCH$_3$ relative to ZR').

Due to their basic character, the compounds I, II, III and IV are capable of forming adducts or salts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid, carbonylic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphonic acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the second main group, in particular calcium and magnesium, and of the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can in this case be in the various valences which they can assume.

When preparing the mixtures, it is preferred to employ the pure active ingredients I, II, III and IV, with which further active ingredients against harmful fungi or other pests such as insects, arachnids or nematodes, or else herbicidal or growth-regulating active ingredients or fertilizers can be admixed, if so desired.

The present invention relates to binary mixtures of compounds I with a compound II, III or IV; however, ternary or quaternary mixtures, which comprise 3 or 4 components, respectively, may also be employed.

A preferred example of three-component mixtures are mixtures of compounds of the formula I, III and IV, where the compounds IV.1, IV.4, IV.5 and IV.10, especially preferably the compound IV.5 (epoxiconazole), are preferred as component IV.

The mixtures of the compounds I and II or III or IV, or the simultaneous joint or separate use of the compounds I, II, III and IV, are distinguished by an outstanding activity against a broad spectrum of phytopathogenic fungi, in particular from the classes of the Ascomycetes, Deuteromycetes, Phycomycetes and Basidiomycetes. Some of them act systemically and can therefore be employed as foliar- and soil-acting fungicides.

They are especially important for controlling a large number of fungi on a variety of crop plants such as cotton, vegetable species (eg. cucumbers, beans and curcubits), barley, grass, oats, coffee, maize, fruit species, rice, rye, soybeans, grapevine, wheat, ornamentals, sugar cane, and a variety of seeds.

They are particularly suitable for controlling the following phytopathogenic fungi: Erysiphe graminis (powdery mildew) on cereals, *Erysiphe cichoracearum* and *Sphaerotheca fuliginea* on curcubits, *Podosphaera leucotricha* on apples, Puccinia species on cereals, Rhizoctonia species on cotton, rice and lawn, Ustilago species on cereals and sugar cane, *Venturia inaequalis* (scab) on apples, Helminthosporium species on cereals, *Septoria nodorum* on wheat, *Botrytis cinera* (gray mold) on strawberries, vegetables, ornamentals and grapevines, *Cercospora arachidicola* on peanuts, *Pseudocercosporella herpotri-*

*choides* on wheat and barley, *Pyricularia oryzae* on rice, *Phytophthora infestans* on potatoes and tomatoes, Pseudoperonospora species on cucurbits and hops, *Plasmopara viticola* on grapevines, Alternaria species on vegetables and fruit, and Fusarium and Verticillium species.

Furthermore, they can be used in the protection of materials (eg. in the protection of wood), for example against *Paecilomyces variotii*.

The compounds I, II, III and IV can be applied simultaneously together or separately or in succession, the sequence, in the case of separate application, generally not having any effect on the result of the control measures.

The compounds I and II are normally used in a weight ratio of from 100:1 to 0.1:1, preferably 70:1 to 5:1, in particular 50:1 to 1:1 (II:I).

The compounds I and III are normally used in a weight ratio of from 10:1 to 0.1:1, preferably 5:1 to 0.5:1, in particular 3:1 to 0.2:1 (III:I).

As a rule, the compounds I and IV are used at a weight ratio of from 10:1 to 0.1:1, preferably 10:1 to 0.2:1, in particular 5:1 to 0.2:1 (IV:I).

The application rates of the mixtures according to the invention are, in the case of the compounds I, from 0.005 to 0.5 kg/ha, preferably 0.005 to 0.5 kg/ha, in particular 0.01 to 0.3 kg/ha, depending on the nature of the desired effect.

Correspondingly, in the case of the compounds II, the application rates are, as a rule, from 0.1 to 10 kg/ha, preferably 0.5 to 5 kg/ha, in particular 1 to 4 kg/ha.

Correspondingly, in the case of the compounds III, the application rates are, as a rule, from 0.01 to 1 kg/ha, preferably 0.05 to 0.5 kg/ha, in particular 0.1 to 0.5 kg/ha.

In the case of the compounds IV, the application rates are generally from 0.01 to 1 kg/ha, preferably 0.05 to 1 kg/ha, in particular 0.05 to 0.5 kg/ha.

For seed treatment, the application rates of the mixture are generally from 0.001 to 100 g/kg seed, preferably 0.01 to 50 g/kg, in particular 0.01 to 10 g/kg.

If phytopathogenic harmful fungi are to be controlled, the separate or joint application of the compounds I and II or III or IV or of the mixtures of the compounds I, II, III and IV is effected by spraying or dusting the seeds, the plants or the soils before or after sowing of the plants, or before or after plant emergence.

The fungicidal synergistic mixtures according to the invention, or the compounds I, II, III and IV, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenyl ether, ethoxylated isooctyl-, octyl- or nonylphenol, alkylphenyl polyglycol ethers or tributylphenyl polyglycol ether, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, ligninsulfite waste liquors or methylcellulose.

Powders, materials for spreading and dusts can be prepared by mixing or jointly grinding the compounds I and II or III or IV or the mixture of the compounds I and II, III or IV with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I, II, III or IV, or of the mixture of the compounds I and II or III or IV. The active ingredients are employed in a purity of from 90% to 100%, preferably 95% to 100% (according to NMR spectrum HPLC.

The compounds I, II, III, or IV or the mixtures, or the corresponding formulations, are applied by treating the harmful fungi or the plants, seeds, soils, areas, materials or spaces to be kept free from them with a fungicidally active amount of the mixture, or of the compounds I, II, III or IV in the case of separate application. Application can be effected before or after infection by the harmful fungi.

The fungicidal activity of the compounds and of the mixtures is demonstrated by the following experiments:

The active ingredients, separately or together, are formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

Evaluation is carried out by determining the infected leaf areas in percent. These percentages are converted into efficacies. The expected efficacies of the mixtures of the active ingredients are determined using Colby's formula [R. S. Colby, Weeds 15, 20–22 (1967)] and compared with the observed efficacies.

Colby's formula:

$$E = x + y + z - x \cdot y \cdot z / 100$$

E expected efficacy, expressed in % of the untreated control, when using the mixture of the active ingredients A, B and C at concentrations of a, b and c x efficacy, expressed in % of the untreated control, when using active ingredient A at a concentration of a y efficacy, expressed in % of the untreated control, when using active ingredient B at a concentration of b z efficacy, expressed in % of the untreated control, when using active ingredient C at a concentration of c The efficacy (w) is calculated as follows using Abbot's formula:

$$w = (1-\alpha) \cdot 100/\beta$$

α is the fungal infection of the treated plants in % and
β is the fungal infection of the untreated (control) plants in %

An efficacy of 0 means that the infection level of the treated plants corresponds to that of the untreated control plants; an efficacy of 100 means that the treated plants are not infected.

EXAMPLES 1–9

Activity Against *Puccinia recondita* on Wheat (leaf rust of wheat)

Leaves of wheat seedlings cv. "Frühgold" in pots were dusted with leaf rust spores (*Puccinia recondita*). The pots were then placed for 24 hours into a chamber at high atmospheric humidity (90 to 95%) and 20 to 22° C. During this time, the spores germinated, and the germination tubes penetrated the plant tissue. The next day, the infected plants were sprayed to run-off with an aqueous spray mixture made with a stock solution of 10% of active ingredient, 63% of cyclohexanone and 27% of emulsifier. After the spray coating had dried on, the test plants were grown in the greenhouse for 7 days at from 20 to 22° C. and a relative atmospheric humidity of 65 to 70%. The extent of rust development on the leaves was then determined.

The visually determined values for the percentage of diseased leaf area were converted into efficacies as % of the untreated control. An efficacy of 0 means the same disease level as in the untreated control. An efficacy of 100 means a disease level of 0%. The expected efficacies for combinations of active ingredients were determined using Colby's formula (Colby, S. R. (Calculating synergistic and antagonistic responses of herbicide combinations", Weeds, 15, p. 20–22, 1967) and compared with the observed efficacies.

TABLE 4

| Active ingredient or combinations | Concentration of active ingredient in the spray mixture in ppm | Efficacy in % of the untreated control |
|---|---|---|
| 1V Control (untreated) | (disease level 100%) | 0 |
| 2V A = Compound No. 1.32 as shown in Table 1 | 4 | 10 |
| 3V B = Compound No. 1.38 as shown in Table 1 | 4 | 30 |
| 4V Compound IIIa | 4 | 0 |
| 5V Compound IIIb | 4 | 0 |

TABLE 5

| Ex. | Concentration of active ingredient in the spray mixture in ppm | Observed efficacy | Calculated efficacy*⁾ |
|---|---|---|---|
| 6 | 4A + 4IIIa | 50 | 10 |
| 7 | 4A + 4IIIa | 30 | 10 |
| 8 | 4B + 4IIIa | 80 | 30 |
| 9 | 4B + 4IIIb | 60 | 30 |

*⁾calculated according to Colby

The test results reveal that the observed efficacy for all mixing ratios exceeds the efficacy precalculated using Colby's formula.

EXAMPLES 10–17

Activity Against Mildew of Wheat

Leaves of wheat seedlings cv. "Frühgold" in pots were sprayed to run-off with an aqueous spray mixture made with a stock solution of 10% of active ingredient, 63% of cyclohexanone and 27% of emulsifier and, 24 hours after the spray coating had dried on, dusted with spores of mildew of wheat (*Erysiphe graminis forma specialis tritici*). The test plants were subsequently placed in a greenhouse at from 20 to 22° C. and a relative atmospheric humidity of 75 to 80%. After 7 days, the extent of mildew development was determined visually as disease level in % of the entire leaf area.

The visually determined values for the percentage of diseased leaf area were converted into efficacies as % of the untreated control. An efficacy of 0 means the same disease level as in the untreated control, an efficacy of 100 means a disease level of 0%. The expected efficacies for combinations of active ingredients were determined using Colby's formula (Colby, S. R. (Calculating synergistic and antagonistic responses of herbicide combinations", Weeds, 15, p. 20–22, 1967) and compared with the observed efficacies.

TABLE 6

| Active ingredient or combinations | Concentration of active ingredient in the spray mixture in ppm | Efficacy in % of the untreated control |
|---|---|---|
| 11V Control (untreated) | (disease level 76%) | 0 |
| 12V A | 4 | 61 |
| 13V B | 4 | 74 |
| 14V Compound IIIa | 4 | 34 |
| 15V Compound IIIc | 4 | 34 |

TABLE 7

| Ex. | Concentration of active ingredient in the spray mixture in ppm | Observed efficacy | Calculated efficacy*⁾ |
|---|---|---|---|
| 16 | 4A + 4IIIb | 93 | 74 |
| 17 | 4B + 4IIIc | 93 | 83 |

*⁾calculated according to Colby

The test results reveal that the observed efficacy for all mixing ratios exceeds the efficacy precalculated using Colby's formula.

EXAMPLES 18–32

Activity Against Mildew of Wheat

Leaves of wheat seedlings cv. "Frühgold" in pots were sprayed to run-off with an aqueous preparation of active ingredient made with a stock solution of 10% of active ingredient, 63% of cyclohexanone and 27% of emulsifier and, 24 hours after the spray coating had dried on, dusted with spores of mildew of wheat (*Erysiphe graminis forma specialis tritici*). The test plants were subsequently placed in a greenhouse at from 20 to 22° C. and a relative atmospheric humidity of 75 to 80%. After 7 days, the extent of mildew development was determined visually as disease level in % of the entire leaf area.

The visually determined values for the percentage of diseased leaf area were converted into efficacies as % of the untreated control, an efficacy of 100 means a disease level of 0%. The expected efficacies for combinations of active ingredients were determined using Colby's formula (Colby, S. R. (Calculating synergistic and antagonistic responses of herbicide combinations", weeds, 15, p. 20–22, 1967) and compared with the observed efficaies.

TABLE 8

| Ex. | Active ingredient | Concentration of active ingredient in the spray mixture in ppm | Efficacy in % of the untreated control |
|---|---|---|---|
| 18V | Control (untreated) | disease level 92%) | 0 |
| 19V | Compound No. 1.32 as shown in Table 1 = A | 1.6<br>0.8 | 14<br>14 |
| 20V | Compound No. 1.38 as shown in Table 1 = B | 1.6<br>0.8 | 0<br>0 |
| 21V | IV.5 = epoxiconazole | 0.8 | 89 |
| 22V | IV.8 = flusilazole | 0.8 | 68 |
| 23V | IV.9 = hexaconazole | 1.6<br>0.8 | 46<br>0 |
| 24V | IV.12 = propiconazole | 0.8 | 0 |

TABLE 9

| Ex. | Concentration of active ingredient in the spray mixture in ppm | Observed efficacy | Calculated efficacy*) |
|---|---|---|---|
| 25 | 0.8 A + 0.8 IV.5 | 98 | 90 |
| 26 | 0.8 + 0.8 IV.B | 95 | 72 |
| 27 | 1.6 A + 1.6 IV.9 | 95 | 53 |
| 28 | 0.8 A + 0.8 IV.12 | 56 | 14 |
| 29 | 0.8 B + 0.8 IV.5 | 98 | 89 |
| 30 | 0.8 B + 0.8 IV.8 | 95 | 68 |
| 31 | 0.8 B + 0.8 IV.9 | 48 | 0 |
| 32 | 0.8 B + 0.8 IV.12 | 37 | 0 |

*)calculated according to Colby

The test results reveal that the observed efficacy for all mixing ratios exceeds the efficacy precalculated using Colby's formula.

We claim:

1. A fungicidal composition comprising synergistically effective amounts of a) a carbamate of formula I

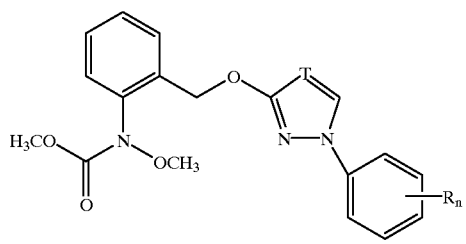

(I)

wherein T is CH or N, n is 0, 1 or 2, and R is halogen, $C_1$–$C_4$-alkyl or $C_1$–$C_4$-haloalkyl, where the radicals R are identical or different if n is 2, and b) an azole IV selected from the group of the compounds IV.1 to IV.17

1-[(2RS,4RS;2RS,4SR)-4-bromo-(2,4-dichlorophenyl) tetrahydrofuryl]-1H-1,2,4-triazole (IV.1)

2-(4-chlorophenyl)-3-cyclopropyl-1-(1H-1,2,4-triazol-1-yl)butan-2-ol (IV.2)

(+)-4-chloro-4-[4-methyl-2-(1H-1,2,4-triazol-1-ylmethyl)-1,3-dioxolan-2-yl]phenyl 4-chlorophenyl ether (IV.3)

(E)-(R,S)-1-(2,4-dichlorophenyl)-4,4-dimethyl-2-(1H-1,2,4-triazol-1-yl)pent-1-en-3-ol (IV.4)

(Z)-2-(1H-1,2,4-triazol-1-ylmethyl)-2-(4-fluorophenyl)-3-(2-chlorophenyl)oxirane (IV.5)

4-(4-chlorophenyl)-2-phenyl-2-(1H-1,2,4-triazolylmethyl)butyronitrile (IV.6)

3-(2,4-dichlorophenyl)-6-fluoro-2-(1H-1,2,4-triazol-1-yl)-quinazolin-4(3H)-one (IV.7)

bis(-4-fluorophenyl)(methyl)(1H-1,2,4-triazol-1-ylmethyl)-silane (IV.8)

(R,S)-2-(2,4-dichlorophenyl)-1-(1H-1,2,4-triazol-1-yl)hexan-2-ol (IV.9)

(1RS,5RS;1RS,5SR)-5-(4-chlorobenzyl)-2,2-dimethyl-1-(1H-1,2,4-triazol-1-ylmethyl)cyclopentanol (IV.10)

N-propyl-N-[2-(2,4,6-trichlorophenoxy)ethyl]imidazol-1-carboxamide (IV.11)

(+)-1-[2-(2,4-dichlorophenyl)-4-propyl-1,3-dioxolan-2-ylme-thyl]-1H-1,2,4-triazole (IV.12)

(R,S)-1-(4-chlorophenyl)-4,4-dimethyl-3-(1H-1,2,4-triazol-1-ylmethyl)pentan-3-ol (IV.13)

(+)-2-(2,4-dichlorophenyl)-3-(1H-1,2,4-triazolyl) propyl 1,1,2,2-tetrafluoroethyl ether (IV.14)

(E)-1-[1-[[4-chloro-2-(trifluoromethyl)phenyl]imino]-2-propoxyethyl]-1H-imidazole (IV.15)

(R,S)-2,4'-difluoro-α-(1H-1,2,4-triazol-1-ylmethyl) benzhydryl alcohol (IV.16)

2-p-chlorophenyl-2-(1H-1,2,4-triazol-1-ylmethyl) hexanonitrile (IV.17).

2. The composition defined in claim 1 comprising one or more of the azole derivatives IV.1, IV.4, IV.5, or IV.10.

3. The composition defined in claim 1, comprising the azole IV and the carbamate I in a weight ratio of from 100:1 to 0.1:1.

4. A method for controlling harmful fungi, which comprises treating the harmful fungi, their environment, or plants, seeds, soils, areas, materials or spaces to be kept free from said fungi with synergistically effective amount of the carbamate of formula I and the azole IV defined in claim 1.

5. The method of claim 4, wherein the carbamate is applied in an amount of from 0.005 to 0.5 kg/ha.

6. The method of claim 4, wherein the azole IV is the compound IV.1, IV.4, IV.5 or IV.10.

7. The method of claim 4, wherein the azole IV is applied in an amount of from 0.1 to 1 kg/ha.

* * * * *

UNITED STATES PATENT AND TRADEMARK OFFICE
CERTIFICATE OF CORRECTION

PATENT NO. : 6,245,792 B1  
DATED : June 12, 2001  
INVENTOR(S) : Mueller et al.

Page 1 of 1

It is certified that error appears in the above-identified patent and that said Letters Patent is hereby corrected as shown below:

<u>Title page,</u>  
ABSTRACT, second line after the formula, "$C_1$-$C_4$-al-kyl" should be -- $C_1$-$C_4$-alkyl --.

<u>Column 14, claim 1,</u>  
Line 31, "ylme- thyl" should be -- ylmethyl --.

Signed and Sealed this

Fifth Day of February, 2002

Attest:

JAMES E. ROGAN
*Attesting Officer*  *Director of the United States Patent and Trademark Office*